(12) United States Patent
Gumaste et al.

(10) Patent No.: US 9,162,031 B2
(45) Date of Patent: Oct. 20, 2015

(54) DIRECTIONAL FLOW SENSOR INHALER

(71) Applicant: MICRODOSE THERAPEUTX, INC., Monmouth Junction, NJ (US)

(72) Inventors: Anand V. Gumaste, West Windsor, NJ (US); John Bowers, Clarksburg, NJ (US)

(73) Assignee: MICRODOSE THERAPEUTX, INC., Monmouth Junction, NJ (US)

( * ) Notice: Subject to any disclaimer, the term of this patent is extended or adjusted under 35 U.S.C. 154(b) by 236 days.

(21) Appl. No.: 13/913,137

(22) Filed: Jun. 7, 2013

(65) Prior Publication Data
US 2013/0291864 A1 Nov. 7, 2013

Related U.S. Application Data

(63) Continuation of application No. 11/064,201, filed on Feb. 23, 2005, now Pat. No. 8,474,452.

(60) Provisional application No. 60/547,324, filed on Feb. 24, 2004.

(51) Int. Cl.
*A61M 16/00* (2006.01)
*A61M 15/00* (2006.01)
*B05D 7/14* (2006.01)
*A61M 15/02* (2006.01)

(52) U.S. Cl.
CPC ....... *A61M 15/0091* (2013.01); *A61M 15/0085* (2013.01); *A61M 15/02* (2013.01); *A61M 2016/0021* (2013.01); *A61M 2202/064* (2013.01); *A61M 2205/3375* (2013.01)

(58) Field of Classification Search
CPC .............. A61M 15/0091; A61M 15/0085; A61M 2205/3375; A61M 15/0005; A61M 15/001; A61M 11/005
USPC ............ 128/204.21, 203.12, 204.23, 204.26, 128/203.25, 203.14, 203.19, 203.21, 128/203.15; 600/529, 533, 537, 538, 586, 600/587
See application file for complete search history.

(56) References Cited

U.S. PATENT DOCUMENTS

| | | | |
|---|---|---|---|
| 2,517,482 A | 8/1950 | Hall | 128/206 |
| 2,965,842 A | 12/1960 | Jacobson | 324/701 |
| 3,507,277 A | 4/1970 | Altouyan et al. | 128/208 |

(Continued)

FOREIGN PATENT DOCUMENTS

| | | | | |
|---|---|---|---|---|
| CA | 2 364 009 | 2/2007 | | A61M 15/00 |
| DE | 102005005540 | 8/2006 | | A61M 15/00 |

(Continued)

OTHER PUBLICATIONS

European Search Report issued in Appln. No. 05713984.2-2320/1718354 PCT/US2005005750, dated May 30, 2011 (5 pgs).

(Continued)

*Primary Examiner* — Kristen Matter
(74) *Attorney, Agent, or Firm* — Hayes Soloway P.C.

(57) ABSTRACT

An fluid sensor to activate and control various components of an inhalation device. The fluid sensor includes an acoustic element, such as a microphone, positioned within said inhalation device to detect fluid within the device and output signals representative of the frequency, direction and/or amplitude of the fluid. These signals control and activate an electrostatic plate and/or a high frequency vibrator.

16 Claims, 5 Drawing Sheets

(56) References Cited

U.S. PATENT DOCUMENTS

| | | | |
|---|---|---|---|
| 3,518,992 A | 7/1970 | Altounyan et al. | 128/208 |
| 3,635,219 A | 1/1972 | Altounyan et al. | 128/266 |
| 3,795,244 A | 3/1974 | Lax et al. | 128/266 |
| 3,807,400 A | 4/1974 | Cocozza | 128/266 |
| 3,831,606 A | 8/1974 | Damani | 128/266 |
| 3,946,726 A | 3/1976 | Pikul | 600/538 |
| 3,948,264 A | 4/1976 | Wilke et al. | 128/266 |
| 4,122,842 A | 10/1978 | Pikul | 128/2.08 |
| 4,733,797 A | 3/1988 | Haber | 221/8 |
| 4,827,922 A | 5/1989 | Champain et al. | 128/204.21 |
| 5,121,639 A | 6/1992 | McShane | 73/861.06 |
| 5,134,890 A | 8/1992 | Abrams | 73/861.52 |
| 5,195,528 A | 3/1993 | Hok | 600/538 |
| 5,201,322 A | 4/1993 | Henry et al. | 600/532 |
| 5,312,281 A | 5/1994 | Takahashi et al. | 446/25 |
| 5,344,043 A | 9/1994 | Moulding et al. | 221/71 |
| 5,458,135 A | 10/1995 | Patton et al. | 128/200 |
| 5,507,277 A | 4/1996 | Rubsamen et al. | 128/200.14 |
| 5,551,416 A | 9/1996 | Stimpson et al. | 128/200 |
| 5,570,682 A | 11/1996 | Johnson | 128/200.14 |
| 5,694,920 A | 12/1997 | Abrams et al. | 128/200.16 |
| 5,735,263 A | 4/1998 | Rubsamen et al. | 128/200.14 |
| 5,749,368 A | 5/1998 | Kase | 600/533 |
| 5,758,637 A | 6/1998 | Ivri et al. | 128/200.16 |
| 5,884,624 A | 3/1999 | Barnett et al. | 128/206.24 |
| 5,906,202 A | 5/1999 | Schuster et al. | 128/203.23 |
| 6,085,740 A | 7/2000 | Ivri et al. | 128/200.16 |
| 6,142,146 A | 11/2000 | Abrams et al. | 128/203.15 |
| 6,152,130 A | 11/2000 | Abrams et al. | 128/204 |
| 6,367,470 B1 | 4/2002 | Denyer et al. | 128/200.14 |
| 6,546,927 B2 | 4/2003 | Litherland et al. | 128/200.16 |
| 6,629,646 B1 | 10/2003 | Ivri | 239/4 |
| 6,889,690 B2 | 5/2005 | Crowder et al. | 128/203.15 |
| 6,978,779 B2 | 12/2005 | Haveri | 128/200.16 |
| 6,985,798 B2 | 1/2006 | Crowder et al. | 700/240 |
| 7,233,228 B2 | 6/2007 | Lintell | 340/309.7 |
| 7,538,473 B2 | 5/2009 | Blandino et al. | 310/317 |
| 7,607,435 B2 | 10/2009 | Lipp | 128/203.13 |
| 7,748,382 B2 | 7/2010 | Denyer et al. | F16K 31/02 |
| 8,474,452 B2 * | 7/2013 | Gumaste et al. | 128/203.15 |
| 2001/0015099 A1 | 8/2001 | Blaine | 73/290 R |
| 2002/0032409 A1 | 3/2002 | Ritsche | 604/154 |
| 2003/0196660 A1 | 10/2003 | Haveri | 128/203.12 |
| 2004/0250812 A1 | 12/2004 | Davies et al. | 128/200.14 |
| 2005/0121027 A1 | 6/2005 | Nilsson et al. | 128/200.23 |
| 2005/0155601 A1 | 7/2005 | Steiner et al. | 128/200.23 |
| 2005/0174216 A1 | 8/2005 | Lintell | 340/309.16 |
| 2005/0267628 A1 | 12/2005 | Crowder et al. | 700/240 |
| 2006/0213503 A1 | 9/2006 | Borgschulte et al. | 128/200.14 |
| 2006/0257327 A1 | 11/2006 | Zierenberg et al. | 424/46 |
| 2007/0137645 A1 | 6/2007 | Eason et al. | 128/203.15 |
| 2009/0020113 A1 | 1/2009 | Watanabe | 128/200.14 |
| 2009/0308390 A1 | 12/2009 | Smutney et al. | 128/203.15 |
| 2010/0139654 A1 | 6/2010 | Thoemmes et al. | 128/203.15 |
| 2010/0252032 A1 | 10/2010 | Thoemmes et al. | 128/200.23 |
| 2011/0041844 A1 | 2/2011 | Dunne | 128/203.12 |

FOREIGN PATENT DOCUMENTS

| | | | |
|---|---|---|---|
| DE | 102009005048 | 7/2010 | A61H 31/02 |
| EP | 0 461 281 | 12/1991 | A61B 5/087 |
| EP | 0 587 380 | 3/1993 | A61M 15/00 |
| EP | 0587380 | 3/1994 | A61M 15/00 |
| EP | 0824023 | 2/1998 | A61M 15/00 |
| EP | 0627266 | 8/1999 | B05B 7/00 |
| EP | 1142600 | 10/2001 | A61M 11/00 |
| EP | 0910421 | 3/2003 | A61M 11/02 |
| EP | 1 499 276 | 1/2005 | A61J 7/00 |
| EP | 1 124 602 | 4/2005 | A61M 11/06 |
| EP | 1 534 366 | 6/2005 | A61M 15/00 |
| EP | 0 799 076 | 9/2005 | A62B 18/00 |
| EP | 1 617 820 | 1/2006 | A61K 47/18 |
| EP | 1 691 781 | 8/2006 | A61J 1/00 |
| EP | 1 713 530 | 10/2006 | A61B 5/08 |
| EP | 1 986 721 | 11/2008 | A61M 15/00 |
| EP | 1 581 291 | 1/2009 | A61M 15/00 |
| EP | 2 054 167 | 5/2009 | B06B 1/02 |
| EP | 1 292 347 | 10/2009 | A61M 15/00 |
| EP | 1 691 783 | 11/2009 | A61K 9/14 |
| EP | 2 162 174 | 3/2010 | A61M 15/00 |
| EP | 2 016 965 | 5/2010 | A61M 11/00 |
| EP | 2 047 881 | 8/2010 | A61M 15/00 |
| EP | 2 234 728 | 10/2010 | A61M 15/00 |
| EP | 1 706 099 | 5/2011 | A61K 9/14 |
| GB | 2320900 | 7/1998 | A61M 15/00 |
| GB | 2 395 437 | 5/2004 | A61M 15/00 |
| GB | 2395437 | 5/2004 | A61M 15/00 |
| JP | 6-190044 | 12/1994 | A61M 15/00 |
| JP | 2002-524107 | 6/2002 | A61M 15/00 |
| JP | 2002524107 | 8/2002 | A61J 3/00 |
| JP | 2002272845 | 9/2002 | A61M 16/00 |
| JP | 2002538902 | 11/2002 | A61M 11/00 |
| WO | 94/17370 | 8/1994 | G01F 1/50 |
| WO | 97/48431 | 12/1997 | A61M 11/06 |
| WO | 98/52633 | 11/1998 | A61M 15/00 |
| WO | 99/63946 | 12/1999 | |
| WO | WO99/64095 | 12/1999 | A61M 15/00 |
| WO | WO9964095 | 12/1999 | A61M 15/00 |
| WO | 00/24445 | 5/2000 | A61M 11/06 |
| WO | 00/38770 | 7/2000 | A61M 11/06 |
| WO | 00/50111 | 8/2000 | A61M 11/00 |
| WO | WO0054828 | 9/2000 | A61M 15/00 |
| WO | 01/58514 | 8/2001 | A61M 15/00 |
| WO | 02/09574 | 2/2002 | |
| WO | 02/058771 | 8/2002 | A61M 15/00 |
| WO | 03/059423 | 7/2003 | A61M 15/00 |
| WO | WO 03/063937 | 8/2003 | A61M 15/00 |
| WO | WO 03/092576 | 11/2003 | A61J 7/04 |
| WO | WO 2004/002394 | 1/2004 | |
| WO | WO 2004/093848 | 11/2004 | A61K 9/16 |
| WO | WO 2005/053646 | 6/2005 | A61K 9/14 |
| WO | WO 2005/074455 | 8/2005 | |
| WO | WO 2007/096111 | 8/2007 | A61M 15/00 |
| WO | WO 2008/021281 | 2/2008 | |
| WO | WO 2009/007068 | 1/2009 | A61M 15/00 |
| WO | WO 2009/090084 | 7/2009 | A61M 15/00 |
| WO | WO 2011/160932 | 12/2011 | A61M 15/00 |
| WO | WO 2011/163272 | 12/2011 | A61M 15/00 |

OTHER PUBLICATIONS

Indian Office Action issued in application No. 3051/CHENP/2006, dated Aug. 26, 2011 (2 pgs).
Israeli Office Action issued in Application No. 10593/0007.000 dated Jun. 2, 2011 (1 pg).
Israeli Office Action issued in application No. 177139, dated Jun. 2, 2011 (1 pg).
Japanese Office Action issued in application No. 2006-554320, dated. May 19, 2011 (10 pgs).
Japanese Office Action, Patent Appln. No. 2006-554320 (drafted Aug. 16, 2010) and English Translation of Action (7 pgs).
Japanese Office Action: Decision of Refusal, issued in application No. 2006-554320, drafted Feb. 1, 2012 (2 pgs).
Mexican Office Action, (dated Sep. 9, 2010) and English Translation of Action (3 pgs).
Russian Office Action, Russian Patent Appln. No. 2006133895, Date=pre-effective filing date.
South Korean Office Action, with translation issued in Appln. No. 2006-7016841, dated Aug. 29, 2011 (9 pgs).

* cited by examiner

DIRECTIONAL FLOW SENSOR INHALER

CROSS REFERENCE TO RELATED APPLICATION

This application is a continuation of U.S. patent application Ser. No. 11/064,201, filed Feb. 23, 2005, which claims priority to co-pending U.S. Provisional Application entitled "Directional Flow Sensor Inhaler", having Ser. No. 60/547,324, Filed Feb. 24, 2004 which is entirely incorporated herein by reference.

TECHNICAL FIELD

The present invention relates generally to the field of inhalation devices, and more specifically, to inhalation devices that utilize acoustic control to facilitate breath activation of different systems of the inhalation device. Particular utility for the present invention is found in the area of facilitating inhalation of powdered medications.

BACKGROUND OF THE INVENTION

Certain diseases of the respiratory tract are known to respond to treatment by the direct application of therapeutic agents. As these agents are most readily available in dry powdered form, their application is most conveniently accomplished by inhaling the powdered material through the nose or mouth. Alternatively, the drug in this form may be used for treatment of diseases other than those of the respiratory system. When the drug is deposited on the very large surface areas of the respiratory tract, it may be very rapidly absorbed into the blood stream; hence, this method of application may take the place of administration by injection, tablet, or other conventional means.

Several inhalation devices useful for dispensing this powder form of medicament are known in the prior art. For example, in U.S. Pat. Nos. 3,507,277; 3,518,992; 3,635,219; 3,795,244; and 3,807,400, inhalation devices are disclosed having means for piercing of a capsule containing a powdered medicament, which upon inhalation is drawn out of the pierced capsule and into the user's mouth and thus, into the user's lungs and respiratory system. Several of these patents disclose propeller means, which upon inhalation aid in dispensing the powder out of the capsule, so that it is not necessary to rely solely on the inhaled air to suction powder from the capsule. For example, in U.S. Pat. No. 2,517,482, issued to Hall, a device is disclosed having a powder-containing capsule, which is pierced by manual depression of a piercing pin by the user. U.S. Pat. No. 3,831,606 discloses an inhalation device having multiple piercing pins, propeller means, and a self-contained power source for operating the propeller means via external manual manipulation, so that upon inhalation the propeller means aids in dispensing the powder into the stream of inhaled air. See also U.S. Pat. No. 5,458,135.

The above description of the prior art is taken largely from U.S. Pat. No. 3,948,264 to Wilke et al, who disclose a device for facilitating inhalation of a powdered medication. A capsule piercing structure is provided, which upon rotation puts one or more holes in the capsule, which contains medication, so that upon vibration of the capsule by an electro-mechanical vibrator, the powdered drug may be released from the capsule. The electromechanical vibrator includes, at its innermost end, a vibrating plunger rod that is connected to a mechanical solenoid buzzer for energizing the rod to vibrate. The buzzer is powered by a high-energy electric cell and is activated by an external button switch. Moreover, as noted above, in Wilke et al.'s disclosed device, vibration of the powder is activated by depressing a push button. This can be difficult and painful for some users (e.g., patients suffering from extreme arthritis). Finally, in order to use Wilke et al.'s disclosed inhaler most efficaciously, the user must depress the vibration-actuating push button at precisely the same time that the user begins inhalation. This can also be difficult for some users (e.g., very young patients, patients suffering from neuromuscular disorders, etc.).

The prior art, such as described above, is dominated by inhaler devices that are activated by some mechanical means of activation, e.g., airflow sensors that include: flapper valves, turbine valves, swirl generators, vortex measurement devices, hot wire, direct pressure drop, ultra sonic, Doppler shift measurement, etc.

In our prior U.S. Pat. No. 6,152,130, issued Nov. 28, 2000, we provide an inhalation device with a fluid sensor to activate and control various components of the device. The fluid sensor includes an acoustic element, such as a microphone, positioned within the inhalation device to detect fluid within the device and output signals representative of the frequency and/or amplitude of the fluid. These signals control and activate an electrostatic plate and/or a high frequency vibrator. This inhalation device provided improved utilization of mediation by ensuring that the full (proper) dosage of the medicament is released when the patient breathes. However, this acoustic sensor flow does not have the ability to detect the direction of the flow of air. If the sensor detects a flow of air while user is exhaling, the medicament could be released at the wrong time and the patient would not receive the full dose.

Thus, a heretofore unaddressed need exists in the industry to address the aforementioned deficiencies and inadequacies.

SUMMARY OF THE INVENTION

The present invention provides an improvement over the prior art inhalation devices such as our aforementioned U.S. Pat. No. 6,152,130. The present invention provides a directional acoustic flow sensor to operate the inhaler. The direction acoustic flow sensor detects the detection of the airflow into the inhaler and permits the activation of the inhaler when the user inhales and not when the user exhales. A preferred embodiment includes an acoustic controller, wherein the acoustic controller includes an acoustic element to sense air flow around the element and for producing signals representative of a frequency, direction and amplitude of the airflow, the signals being used to control (e.g., activate, deactivate, apply incremental voltage, etc.) certain components of the inhalation device. This feature helps make the inhaler more user friendly, minimizes training necessary to use the device and improves usability for children.

Preferably, the acoustic element is a microphone element or pressure transducer positioned within the air passage of an inhalation device, (e.g., a dry powder inhaler) that produces signals in response to the inhalation air flow. These signals are used to control certain components of the inhaler, e.g., a high frequency vibrator, an electrostatic plate, timer, counter, etc. Also preferably, these signals are used to activate/control certain components of the inhalation device to maximize the inhalation effectiveness to obtain maximum patient benefit from the medicament.

Thus, the present invention provides a fully automated inhalation device, which is activated on inhalation only, that permits optimal utilization of the particular medication. For example, acoustic signals can be used to trigger the high frequency vibrator only when the patient has achieved optimum (e.g., maximum) inhalation effort, thereby ensuring that the full (proper) dosage of medicament properly enters the patient's respiratory system. Alternatively, these signals (breath-activated signals) can be used to progressively apply increasing power to, or, sequentially activate/deactivate the various components of the inhalation device to achieve optimal inhalation dosage.

It will be appreciated by those skilled in the art that although the following Detailed Description will proceed with reference being made to preferred embodiments and methods of use, the present invention is not intended to be limited to these preferred embodiments and methods of use. Rather, the present invention is of broad scope and is intended to be limited as only set forth in the accompanying claims.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. In the drawings, like reference numerals designate corresponding parts throughout the several views.

DETAILED DESCRIPTION

Figure 1:
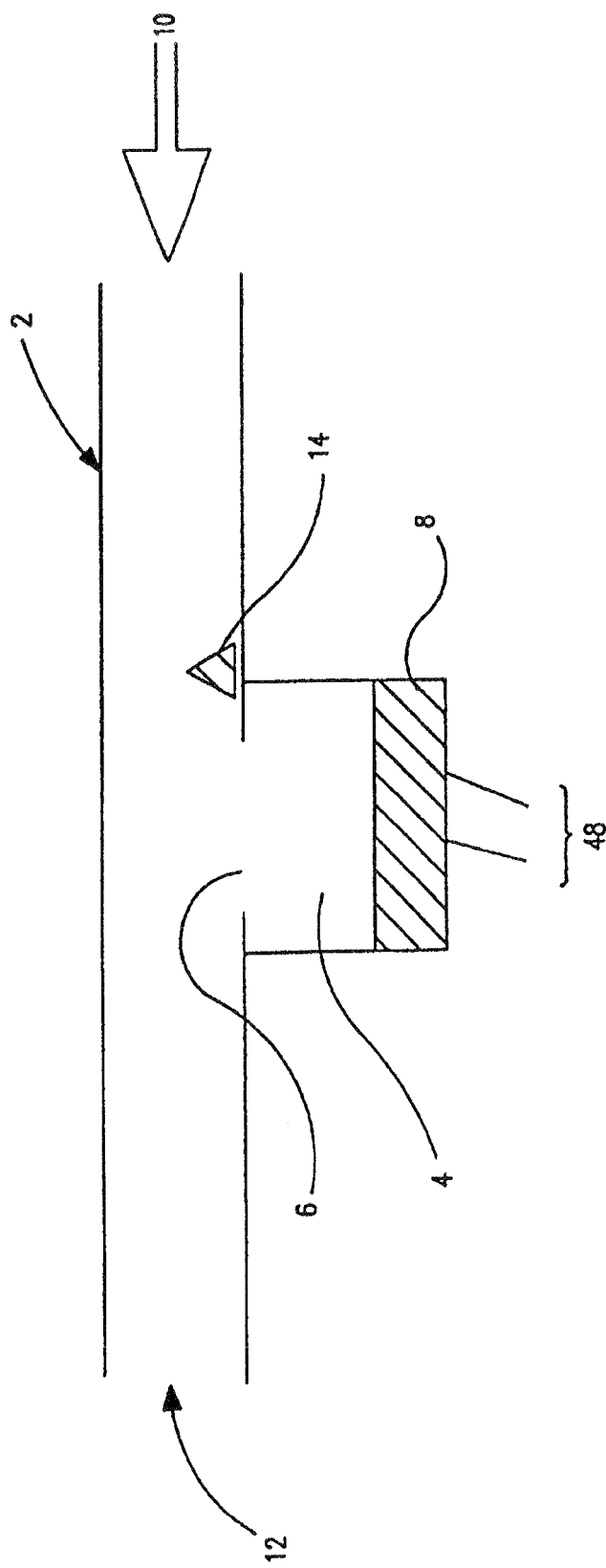
FIG. 1 is a cross-sectional view of a typical inhalation device and the acoustic controller of the present invention.
Figure 2:
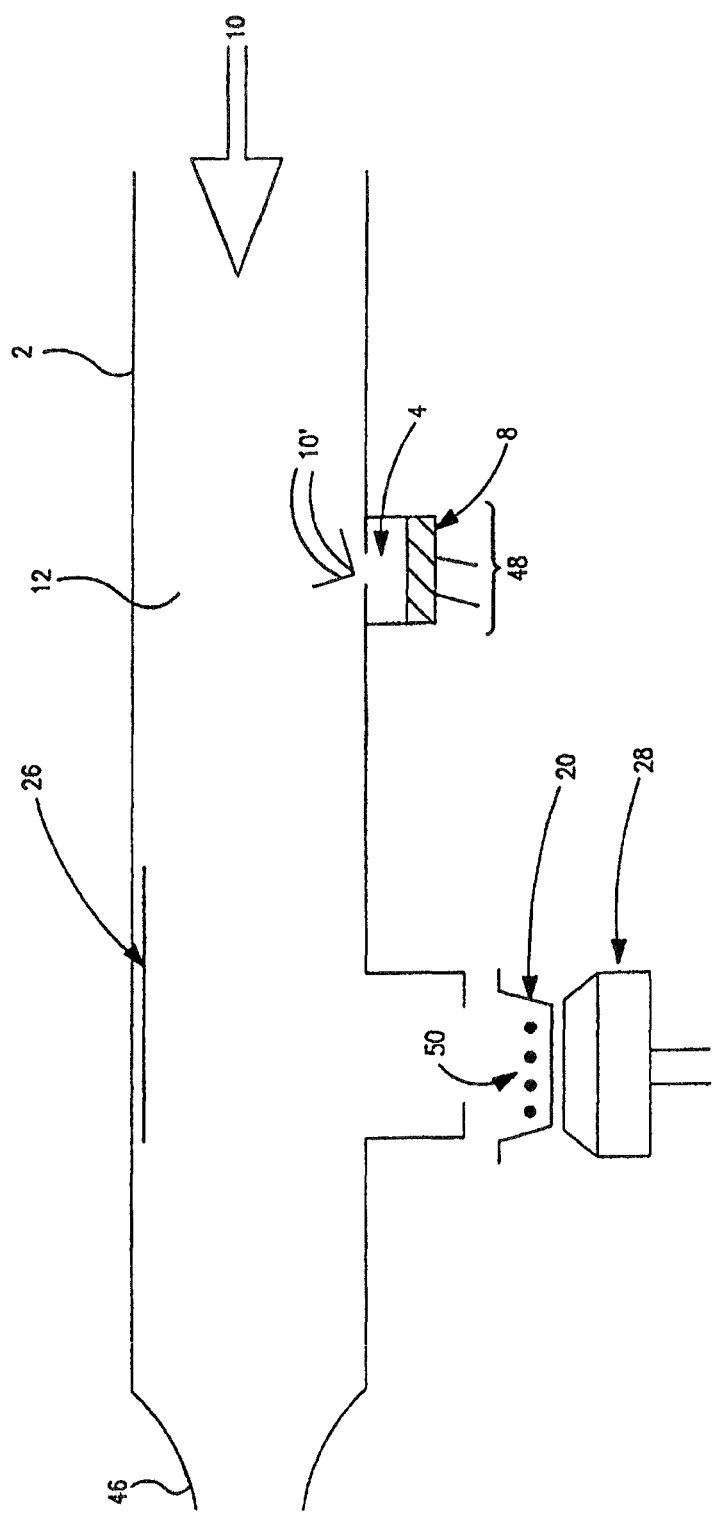
FIG. 2 is an expanded cross-sectional view of FIG. 1.

Referring to FIGS. 1 and 2, a cross-sectional view of an airflow passage 12 of an inhalation device 2 is depicted. It should be noted at the outset that the airflow passage 12 depicted in FIG. 1 is a generalized airflow passage of a typical inhalation device, such as those discussed above. However, the present invention is intended to be adapted to any inhalation device, regardless of the particular geometry of the airflow passage. At its most basic level, the present invention operates by providing an air flow sensor 8 to detect air flow turbulence around the sensor 8 (i.e., inspiratory air flow rate of a user of the inhaler) and to control various components of the inhalation device 2, as a function of the amplitude, direction and/or frequency of the detected airflow turbulence, as described below.

As shown in FIG. 1, air 10 (or any other fluid) enters the airflow passageway 12, typically by the respiratory activity of a patient inhaling on the device 2. As air 10 flows through the passage 12, a portion thereof flows through the opening 6 in the passage 2 into a cavity 4. Placed within the cavity 4 is an air flow-sensing device 8. Preferably, the airflow-sensing device 8 is an acoustic sensing element, e.g. a microphone. Also preferably, microphone 8 is adapted to produce an appropriate noise signal 48 in response to the airflow detected within the cavity 4. The amplitude, direction, and frequency of the airflow within the cavity 4 are a function of the airflow rate 10 within the air passage 12 of the device 2. Thus, output noise signals 48 from the microphone 8 will vary in both frequency and amplitude as a function of air flow rate and direction within the cavity (which is a function of flow rate within the passage 12), and thus, can be used to control various components of the inhaler 2 as a function of frequency and/or amplitude, as described below. The shape of the cavity 4 and the size of the opening 6 should be chosen in accordance the particular geometry of the air passage 12, the air flow rate 10 through the passage 12, and/or the frequency response and/or sensitivity of the microphone 8; and all such variations are within the scope of the present invention. Preferably, as noted above, the shape of the cavity 4 and the size of the opening 6 are chosen to permit at least a portion of the air within the passage 2 to enter the cavity 4 with sufficient amplitude to induce a response from the microphone 8.

Referring now to FIG. 2, an expanded cross-sectional view of an embodiment of the air flow sensor (described with reference to FIG. 1, above) in a dry powder inhaler, such as disclosed in U.S. Pat. No. 5,694,920. Depicted in FIG. 2 are the components of a typically dry powder inhaler 2. A mouthpiece 46 is provided for a user (i.e., patient) to inhale on the device 2. A high-frequency vibratory mechanism 28 (e.g., piezoelectric element, ultrasonic acoustic transducer, or other electro/mechanical vibratory mechanism, etc.) is provided to vibrate a container 20 (e.g., blister or capsule) of dry powdered medicament 50 to suspend particles of the medicament into the air passage 12. To further aid the suspension of particles, an electrostatic potential plate 26 may be provided to draw particles of a certain charge (i.e., a charge opposite to that of the electrostatic plate 26) into the air stream 10. In this embodiment, a portion 10' of the air 10 drawn into the air passage 12 is induced into the cavity 4, to be detected by the microphone element 8. Upon detection of airflow, the microphone element produces a noise signals 48. The noise signals 48 are used to control either the high-frequency vibrator 28 and/or the electrostatic plate 26, or other components of the inhaler, as described below.

Figure 3:
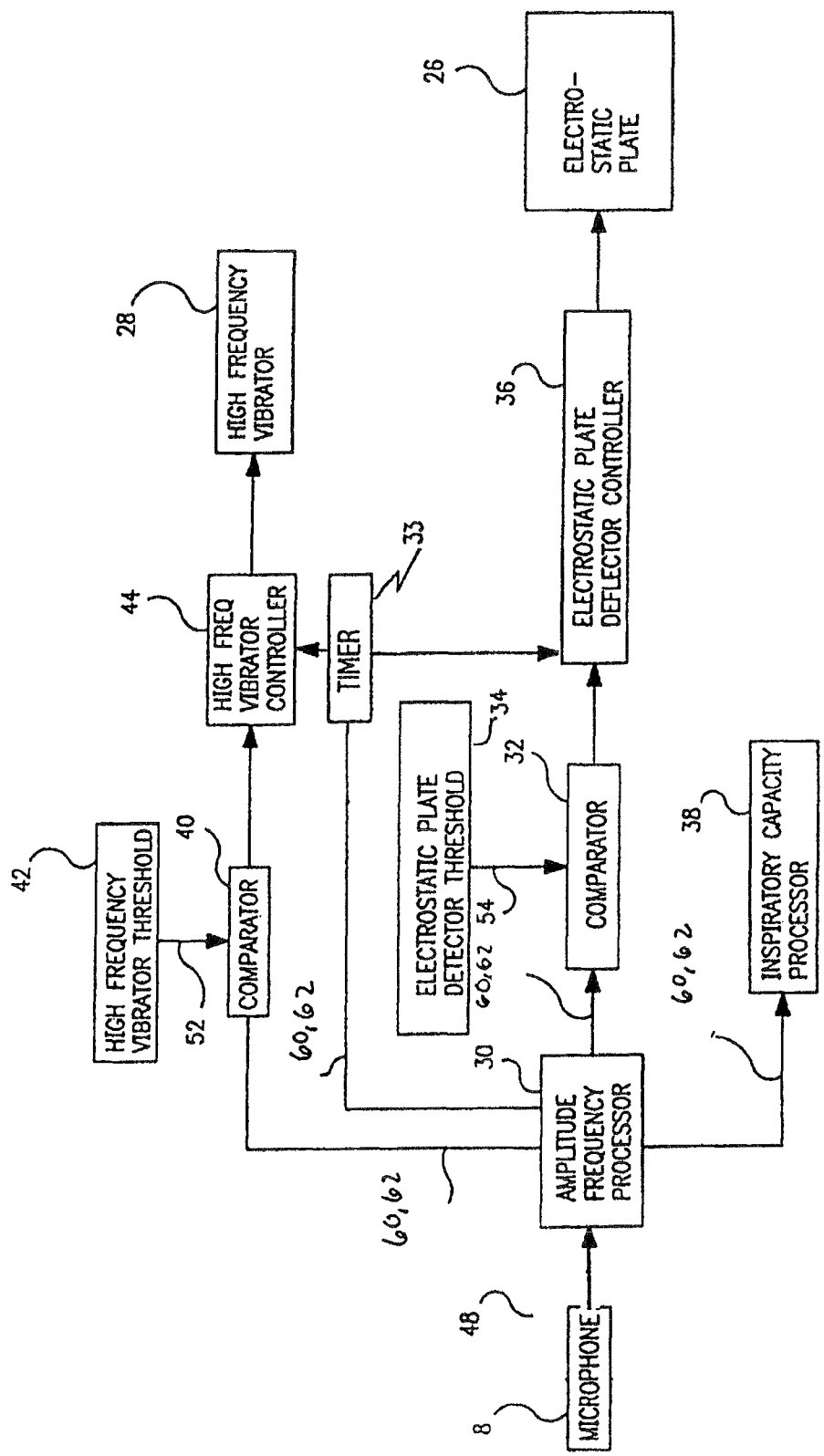
FIG. 3 is a functional block diagram of a preferred embodiment of the directional acoustic controller of the present invention.

FIG. 3 is a block diagram representation of the acoustic control system of the present invention for a dry powder inhaler. As described above, the microphone element 8 produces noise signals 48 in response to detected airflow 10'. These signals are processed by an processing circuit 30 to condition the signals 48 and to determine the direction of the airflow and amplitude, and/or frequency of the noise signals 48. The processor circuit 30 produces two signals: BREATH signal 60 and INHALE signal 62.

Figure 5:
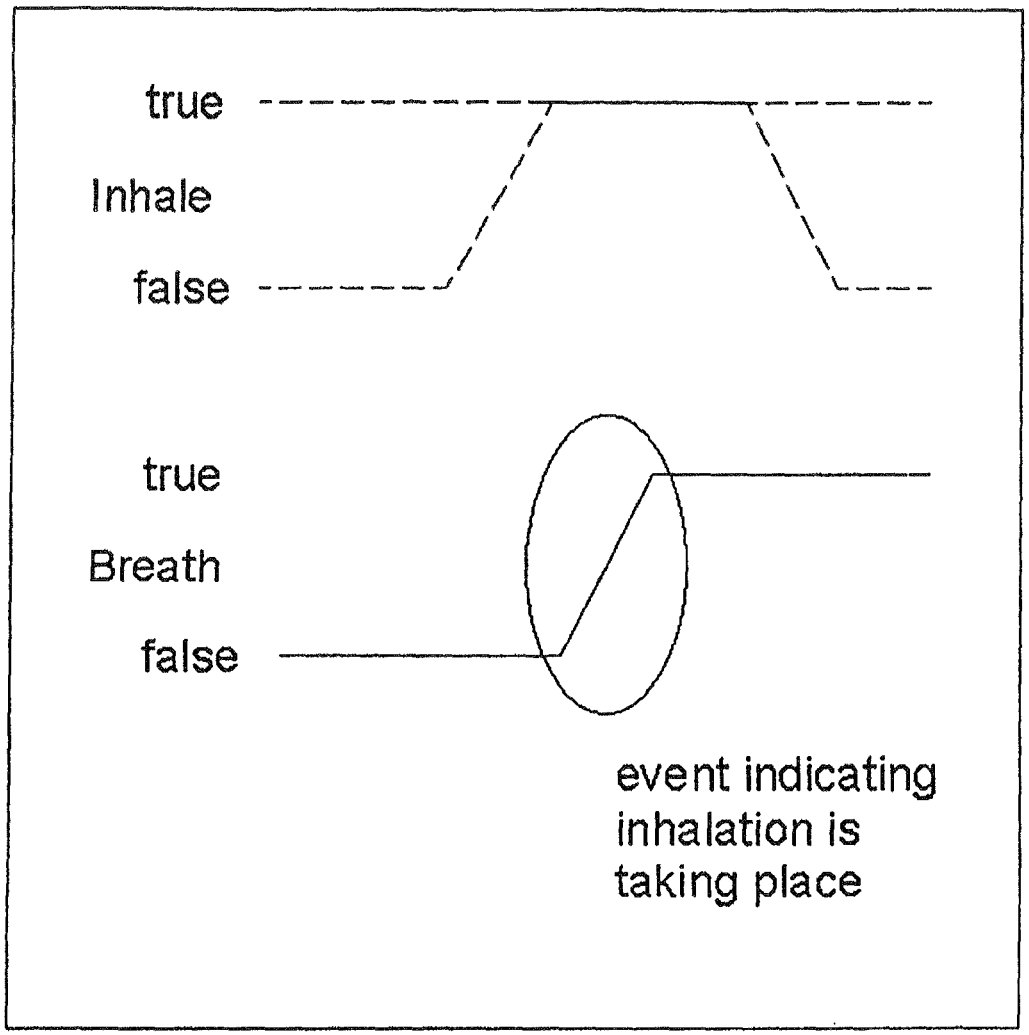
FIG. 5 is a timing diagram for the directional acoustic circuit.

The BREATH signal 60 is a logic level signal that indicates the presence of an airflow in the inhalation device. The INHALE signal 62 is latched at the rising edge of the BREATH signal 60 as an indicator of the direction of the airflow. The state of the INHALE signal at the rising edge of the BREATH signal is a reliable indicator of the direction of the airflow in the channel during breathing. These signals are used to control the high-frequency vibrator and/or electrostatic plate. To that end, BREATH signal 60 is input into a comparator circuit 40 and/or 32 and compared with a reference threshold signal 52 and/or 54, respectively. Furthermore, when the comparator circuit 40 and/or 32 first detects a rising edge on the BREATH signal 60, the INHALE signal 62 is latched by the comparator circuit 40 and/or 32. The high frequency vibrator threshold 42 produces a signal 52 which represents the minimum voltage and/or frequency required to activate the high frequency vibrator controller 44 (which, in turn, activates the high frequency vibrator 26). Comparator 40 compares signal 52 with BREATH signal 60 and if the signals have equal amplitude and/or frequency (within some predetermined error margin) and the latched INHALE signal 62 is true, the comparator 40 activates the high frequency vibrator controller 44, which activates and directly controls the high frequency vibrator 26, as shown in FIG. 5. That is, if the BREATH signal 60 is above a reference threshold, sufficient airflow exists in the air passage 12 to signify breathing. Thus, the combination of the latched INHALE signal 62 being true and the BREATH signal 60 being above a reference threshold (i.e. true) indicates that the user is inhaling. Similarly, a electrostatic plate deflector controller 36 is activated by an equal match of BREATH signal 60 and signal 54 by the comparator 32 and a INHALE signal 62 which is true. Electrostatic plate detector threshold 34 produces signal 54 which represents the minimum voltage and/or frequency required to activate the electrostatic plate 26.

Figure 4:
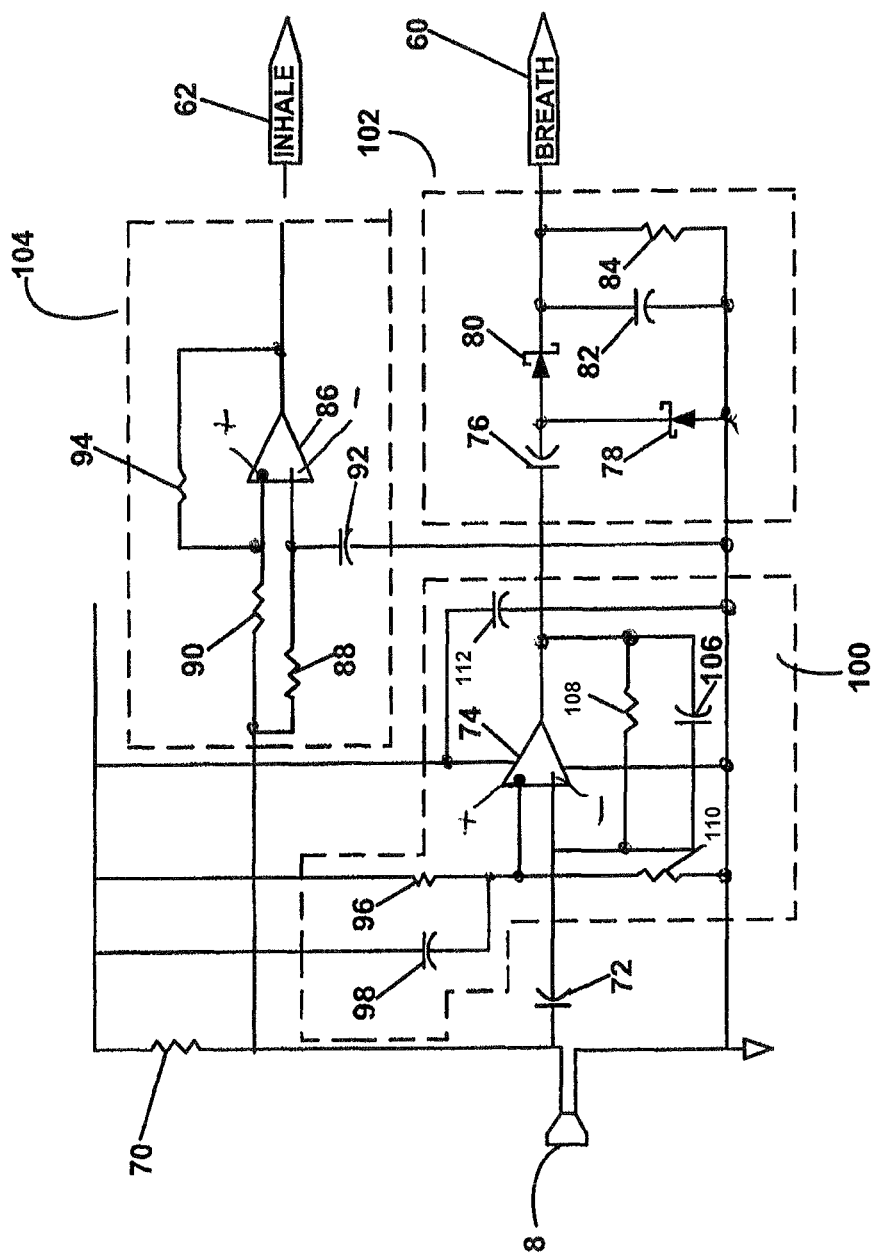
FIG. 4 is a schematic diagram of the directional acoustic circuit.

The high frequency vibrator controller 44 and/or electrostatic plate controller 36 assumes inhalation to be continuing as long as the BREATH signal 60 remains true, independent of the subsequent changes of the INHALE signal 62. Upon the BREATH signal 60 becoming false i.e. the signal falling below the threshold voltage, the high frequency vibrator 28 and/or the electrostatic plate deflector 26 are deactivated FIG. 4 is a schematic diagram including the microphone and the processor circuit. Power to the microphone 8 used in the inhalation device is supplied via resistor 70. In this circuit, the noise signal 48 created by air flow across the microphone 8 is communicated from the microphone via capacitor 72 and amplified by the amplification circuit 100. The amplification circuit consists of op-amp 74 and its associated components, resistor 96, capacitor 98, capacitor 106, resistor 108, resistor 110 and capacitor 112. This amplification circuit 100 also provides low pass filtering to reduce the sensitivity to unwanted signals. Capacitor 76, diode 78, diode 80, capacitor 82 and resistor 84 comprise a rectification circuit 102 that outputs a logic level signal, BREATH, that is indicative of the presence of inhalation. The comparator circuit 104 comprises an op-amp 86, resistor 88, resistor 90, capacitor 92, and resistor 94. The comparator circuit 104 is a comparator that detects the initial direction of the airflow within the channel and outputs a signal INHALE.

The comparator circuit works as follows: Signal 48 is applied, via a low pass filter (70, 72 and the virtual ground of 74), to the comparator. When breathing commences, signal 48 will have an instantaneous voltage offset, relative to the voltage when there is no breathing, due to the change of the pressure in air flow passage 12. The comparator senses this voltage offset by comparing the instantaneous voltage of signal 48 with respect to a long term or low pass filtered version of signal 48, i.e., the signal created at the intersection of resistor 88 and capacitor 92. At the instant when breathing commences, the difference between these two signals represents the direction of the breathing, whether it is an inhalation or exhalation. This difference is sensed by comparator 86 which generates the INHALE signal 62. Other schemes or circuits that exploit the difference between the instantaneous offset of the acoustic sensor signal at the commencement of breathing are within the spirit and scope of the present invention.

It should be understood that noise signal 48 is indicative of the airflow rate and direction 10, described above. The present invention preferably is intended to be controllable as a function of frequency and/or amplitude of noise signals 48, thus, processor circuit can be adapted to condition the noise signals 48 in terms of amplitude or frequency are both.

Another feature of this invention is an improved means for handling tidal delivery of the medicament. Some users need multiple breaths to inhale the prescribed dosage of medicament because of asthma, decreased lung capacity, etc. In this situation, the inhaler will manage the dosage as follows: at such time as the velocity of the air flow of an inhalation decreases below a threshold (the inhalation signal becomes false), dosing pauses; upon the beginning of another inhalation (both the INHALE signal and the BREATH signal become true) dosing continues until either 1) the dosing is complete or 2) the air flow velocity falls below the aforementioned threshold. This process continues until dosing is complete or the cumulative time spent inhaling exceeds a predetermined limit.

Inspiratory capacity processor 38 is provided to compute the peak inspiratory flow 10 (represented by signals 48) of the patient. Although not shown in the drawings, this information can be used to adjust the threshold signals of the high frequency vibrator threshold 42 and/or electrostatic plate detector threshold 34. Of course, to accomplish this, the high frequency vibrator threshold 42 and/or electrostatic plate detector threshold 34 must be programmable, as is known in the art. In this way, the microphone 8 can be programmed to trigger the various components of the inhaler to adjust for varying inspiration flow rates from patient-to-patient or individually. Thus, for example, the inspirator control scheme of the present invention can be self-adjusting to account for a patient's decrease in inspiratory flow rate caused by, for example, decreased lung capacity. Alternatively, the processor 38 can be modified to sequentially turn on the various components herein described (e.g., vibrator, electrostatic plate, etc.) at optimal inhalation times (e.g., peak inhalation effort). Thus, for example, the processor 38 can be modified to activate the vibrator at a time just prior to the user's peak inhalation effort, then to activate the electrostatic plate subsequently, thereby inducing the medicament into the airstream at a time that produces optimal respiratory absorption of the medicament. Moreover, processor 38 can be adapted with appropriate memory to track a patient's inspiratory flow rate, which can be used to adjust the powdered medicament 50 to achieve maximum medication benefit.

Thus, it is evident that there has been provided an inhalation device with acoustic control and method for operating same that fully satisfy both the aims and objectives hereinbefore set forth. It will be appreciated that although specific embodiments and methods of use have been presented, many modifications, alternatives and equivalents are possible. For example, processing circuit 30, threshold signal generators 34 and 42, comparators 42 and 32 and can be any known digital (e.g., microprocessor) or analog circuitry and/or associated software to accomplish the functionality described herein. Although the various components described in FIG. 3 have been described in a modular fashion, each of these components can be discrete off-the-shelf or custom components, or can be included in a single, unified system.

Also, the thresholding circuits 42 and 34, the amplitude/frequency processor 30 and the inspiratory capacitor processor 38 can be adapted to permit user (patient) control and user-definable presets (i.e., minimum flow rate for activation, etc).

In addition, comparators 40 and 32 can be adapted to permit generation of activation signals based differing signal strengths and/or frequency. Thus, for example, the high frequency vibrator can be adapted to activate only when a signal frequency of 1 Khz is achieved, while the electrostatic plate will only activate when a signal strength of 35 mV. is obtained.

Other modifications are also possible. For example, the microphone 8 can be positioned directly on the inner wall of the airflow passage 12 of the device 2, instead of within the cavity 4. In addition, as shown in FIG. 1, a turbulence generator 14 can be provided to generator air turbulence within the air passage 12. This modification, for example, can be used in an inhalation device that would otherwise not permit a portion 10' of the air 10 to enter the cavity 4. In addition, instead of a microphone 8, the acoustic element can be any known fluid pressure transducer (e.g., air pressure transducer)

that will output appropriate signals as a function of fluid pressure (amplitude) and/or frequency. Accordingly, the present invention can be appropriately modified to operate in any fluid medium (other than air), to provide automatic acoustic control.

Still other modifications are possible. For example, although not shown in the drawings, the present invention can be provided with a timer that is controlled by signals 60 and 62. The timer can be appropriately modified to control a schedule of when the device may be activated, to avoid, for example, an overdose. Thus, for example, the timer may be modified to only permit activation of the components of the device at certain times of the day. Moreover, the timer may be appropriately modified to permit downloading of data related to usage (e.g., time of day used, dosage of medicament, inhalation effort, etc.). This data can be particularly relevant for clinical trials where it is important to track the recommended dosage and times of medication. Of course, the previous description could be accomplished with a counter, or the like, that simply counts the amount of times that the device has been used. Furthermore, the counter may be used to track the cumulative time a user has used the device during a particular dosing or over a fixed length of time.

Although the present invention has been directed to an acoustic control scheme for a dry powder inhaler 2, the present invention is not so limited. On the contrary, the present invention is intended to be adapted for any inhalation device that would require a control mechanism (such as described herein) based breath (inhalation) detection. For example, an anesthetic device could be modified with the breath sensor and controller as provided herein to monitor and control the amount of anesthetic a patient receives. Additionally, the acoustic sensing element can be used to measure peak inspiratory and/or expiratory flow of a particular patient, and record this information for downloading and analysis.

Although the preceding detailed description has provided several embodiments of controlling various components of an inhalation device using acoustic signals representative of the amplitude, direction and/or frequency of inhalation, these have been provided only as examples of achieving an acoustic control scheme, and other alternatives are possible without departing substantially from the spirit and principles of the invention. All such modifications and variations are intended to be included herein within the scope of this disclosure and the present invention and protected by the following claims.

We claim:

1. An inhalation device for delivering powdered medicament to a user comprising:
    an air flow passage;
    an acoustic controller including an acoustic sensing element positioned within said air flow passage, said controller being configured to detect air flow around said acoustic sensing element and to produce signals representative of a frequency, amplitude and direction of said air flow; and
    a high frequency vibrator for inducing said powdered medicament into said airflow,
    wherein said high frequency vibrator is adapted to be activated when said signal indicates inhalation and to be deactivated when said signal indicates inhalation has ceased.

2. An inhalation device as claimed in claim 1, wherein said high frequency vibrator is turned on and off a plurality of times until a prescribed amount of powdered medicament is delivered.

3. An inhalation device as claimed in claim 1, wherein said signals control activation of a timer, said timer tracks cumulative inhalation time.

4. An inhalation device as claimed in claim 1, wherein said medicament is delivered from a container.

5. An airflow directional inhalation sensor comprising:
    an acoustic sensing element configured to create a signal when air flows around said acoustic sensing element and
    a conversion circuit to convert said signal into information regarding direction and amplitude of said airflow, wherein said conversion circuit processes said signal to identify a rising edge on a waveform of the signal and determines a direction of the airflow from the identification of the rising edge.

6. A directional inhalation sensor device as claimed in claim 5, wherein said conversion circuit includes a comparator circuit for detecting an initial direction of said airflow.

7. A directional inhalation sensor device as claimed in claim 5, wherein said conversion circuit includes a rectification circuit for detecting presence of said air flow.

8. An air inhalation device for delivering medicament to a user, said device comprising:
    an acoustic controller, said acoustic controller including an acoustic sensing element configured to detect airflow around said acoustic sensing element and to produce signals that identify a direction and amplitude of said airflow;
    a high frequency vibrator configured for inducing said medicament into said airflow when said signals indicate inhalation by said user; and
    a conversion circuit configured to convert said signals into information regarding direction and amplitude of said airflow, wherein said conversion circuit includes a rectification circuit for detecting presence of airflow in said inhalation device, and wherein said conversion circuit processes said signal to identify a rising edge on a waveform of the signal and determines a direction of the airflow from the identification of the rising edge.

9. An inhalation device as claimed in claim 8, wherein said acoustic controller is adapted to stop the vibration of said high frequency vibrator when said signal indicates inhalation has stopped.

10. An inhalation device as claimed in claim 9, wherein said high frequency vibrator is adapted to turn off and on with amplitude of airflow.

11. An inhalation device as claimed in claim 8, wherein said signals control activation of a timer, and said timer tracks cumulative inhalation time.

12. An inhalation device as claimed in claim 11, wherein said timer is adapted to provide feedback to said user when cumulative inhalation time exceeds a predetermined level.

13. An inhalation device as claimed in claim 8, wherein said acoustic sensing element comprises an acoustic microphone element.

14. An inhalation device as claimed in claim 8, wherein said acoustic sensing element comprises an air pressure transducer.

15. An inhalation device as claimed in claim 8, wherein said medicament comprises a dry powder medicament.

16. An inhalation device as claimed in claim 8, wherein said medicament is delivered from a container.

* * * * *